United States Patent
Duncan et al.

(10) Patent No.: US 9,308,008 B2
(45) Date of Patent: Apr. 12, 2016

(54) SURGICAL BAG DEVICE AND REMOTE OPERATING MECHANISM

(71) Applicant: Cook Medical Technologies, LLC, Bloomington, IN (US)

(72) Inventors: Kate Duncan, Mooresville, IN (US); Shawn L. Nichols, Bloomington, IN (US); Scott K. Philhower, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 170 days.

(21) Appl. No.: 14/104,112

(22) Filed: Dec. 12, 2013

(65) Prior Publication Data

US 2014/0180303 A1 Jun. 26, 2014

Related U.S. Application Data

(60) Provisional application No. 61/745,004, filed on Dec. 21, 2012.

(51) Int. Cl.
*A61B 17/221* (2006.01)
*A61B 17/00* (2006.01)
*A61B 17/29* (2006.01)

(52) U.S. Cl.
CPC .......... *A61B 17/221* (2013.01); *A61B 17/00234* (2013.01); *A61B 17/2909* (2013.01); *A61B 2017/00287* (2013.01); *A61B 2017/00867* (2013.01); *A61B 2017/2923* (2013.01)

(58) Field of Classification Search
CPC ........... A61B 17/00234; A61B 17/221; A61B 17/2909; A61B 2017/00287; A61B 2017/00867; A61B 2017/2923; A61B 2017/304; A61B 2017/305
See application file for complete search history.

(56) References Cited

U.S. PATENT DOCUMENTS

| 5,037,379 A | 8/1991 | Clayman et al. |
| 5,074,867 A | 12/1991 | Wilk |

(Continued)

FOREIGN PATENT DOCUMENTS

| WO | WO 2005/025427 A1 | 3/2005 |
| WO | WO 2007/048085 A2 | 4/2007 |

OTHER PUBLICATIONS

International Preliminary Report and Written Opinion for PCT/US2013/074564; dated Jul. 2, 2015, 12 pp.

(Continued)

*Primary Examiner* — Julie A Szpira
(74) *Attorney, Agent, or Firm* — Brinks Gilson & Lione

(57) ABSTRACT

A surgical bag device is provided. The device includes a surgical bag with a pocket at the open top and elongate biasing member disposed in conjunction with the pocket and translatable between a first open position where the biasing member extends through a substantial portion of a circumference of the pocket, to a second closed position. An elongate push rod with a distal end portion is fixed to the biasing member and an opposite proximal end portion operatively engaged with a movable plunger within a housing. The push rod is translatable as urged by the plunger between a distal position extending the biasing member into the pocket and a proximal position withdrawing the biasing member from the pocket. The push rod comprises a plurality of longitudinally spaced teeth disposed thereon, which are meshingly engagable with a plurality of teeth from a corresponding first set of teeth of a pinion gear.

20 Claims, 12 Drawing Sheets

(56) References Cited

U.S. PATENT DOCUMENTS

| | | | |
|---|---|---|---|
| 5,147,371 A | 9/1992 | Washington et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,192,284 A | 3/1993 | Pleatman | |
| 5,192,286 A | 3/1993 | Phan et al. | |
| 5,201,740 A | 4/1993 | Nakao et al. | |
| 5,279,539 A | 1/1994 | Bohan et al. | |
| 5,308,327 A | 5/1994 | Heaven et al. | |
| 5,311,858 A | 5/1994 | Adair | |
| 5,312,416 A | 5/1994 | Spaeth et al. | |
| 5,336,227 A | 8/1994 | Nakao et al. | |
| 5,337,754 A | 8/1994 | Heaven et al. | |
| 5,341,815 A | 8/1994 | Cofone et al. | |
| 5,352,184 A | 10/1994 | Goldberg et al. | |
| 5,354,303 A | 10/1994 | Spaeth et al. | |
| 5,368,597 A | 11/1994 | Pagedas | |
| 5,374,273 A | 12/1994 | Nakao et al. | |
| 5,417,697 A | 5/1995 | Wilk et al. | |
| 5,465,731 A * | 11/1995 | Bell et al. | 600/562 |
| 5,480,404 A | 1/1996 | Kammerer et al. | |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,601,572 A | 2/1997 | Middleman et al. | |
| 5,611,803 A | 3/1997 | Heaven et al. | |
| 5,643,283 A | 7/1997 | Younker | |
| 5,647,372 A | 7/1997 | Tovey et al. | |
| 5,681,324 A | 10/1997 | Kammerer et al. | |
| 5,720,754 A | 2/1998 | Middleman et al. | |
| 5,735,289 A | 4/1998 | Pfeffer et al. | |
| 5,779,716 A | 7/1998 | Cano et al. | |
| 5,971,995 A | 10/1999 | Rousseau | |
| 6,004,330 A | 12/1999 | Middleman et al. | |
| 6,059,793 A | 5/2000 | Pagedas | |
| 6,168,604 B1 | 1/2001 | Cano | |
| 6,206,889 B1 | 3/2001 | Bennardo | |
| 6,228,095 B1 | 5/2001 | Dennis | |
| 6,258,102 B1 | 7/2001 | Pagedas | |
| 6,264,663 B1 | 7/2001 | Cano | |
| 6,348,056 B1 | 2/2002 | Bates et al. | |
| 6,383,197 B1 | 5/2002 | Conlon et al. | |
| 6,387,102 B2 | 5/2002 | Pagedas | |
| 6,419,639 B2 | 7/2002 | Walther et al. | |
| 6,447,523 B1 | 9/2002 | Middleman et al. | |
| 6,685,628 B2 | 2/2004 | Vu | |
| 6,814,739 B2 | 11/2004 | Secrest et al. | |
| 6,971,988 B2 | 12/2005 | Orban, III | |
| 7,044,956 B2 | 5/2006 | Vetter et al. | |
| 7,056,328 B2 | 6/2006 | Arnott | |
| 7,270,663 B2 | 9/2007 | Nakao | |
| 7,387,632 B2 | 6/2008 | Ouchi | |
| 7,547,310 B2 | 6/2009 | Whitfield | |
| 7,618,437 B2 | 11/2009 | Nakao | |
| 7,670,346 B2 | 3/2010 | Whitfield | |
| 7,717,924 B2 | 5/2010 | Bates | |
| 7,722,626 B2 | 5/2010 | Middleman et al. | |
| 7,727,253 B2 | 6/2010 | Ackerman et al. | |
| 8,057,485 B2 | 11/2011 | Hollis et al. | |
| 2002/0019594 A1 | 2/2002 | McClellan et al. | |
| 2004/0138587 A1 | 7/2004 | Lyons, IV | |
| 2004/0158261 A1 | 8/2004 | Vu | |
| 2004/0199159 A1 | 10/2004 | Lee et al. | |
| 2005/0085808 A1 | 4/2005 | Nakao | |
| 2005/0267489 A1 | 12/2005 | Secrest et al. | |
| 2006/0200169 A1 | 9/2006 | Sniffin | |
| 2006/0229639 A1 | 10/2006 | Whitfield | |
| 2006/0229640 A1 | 10/2006 | Whitfield | |
| 2007/0073251 A1 | 3/2007 | Zhou et al. | |
| 2007/0088370 A1 * | 4/2007 | Kahle et al. | 606/114 |
| 2008/0221588 A1 | 9/2008 | Hollis et al. | |
| 2008/0234696 A1 | 9/2008 | Taylor et al. | |
| 2008/0306336 A1 | 12/2008 | Kaye et al. | |
| 2008/0312496 A1 | 12/2008 | Zwolinski | |
| 2009/0082779 A1 | 3/2009 | Nakao | |
| 2009/0192510 A1 | 7/2009 | Bahney | |
| 2009/0306683 A1 | 12/2009 | Zwolinski et al. | |
| 2010/0106052 A1 | 4/2010 | Uznanski et al. | |
| 2010/0152746 A1 | 6/2010 | Ceniccola et al. | |
| 2010/0219091 A1 | 9/2010 | Turner | |
| 2010/0249646 A1 | 9/2010 | Wynne et al. | |
| 2011/0087235 A1 | 4/2011 | Taylor et al. | |
| 2011/0184436 A1 | 7/2011 | Shelton, IV et al. | |
| 2011/0276049 A1 * | 11/2011 | Gerhardt | 606/45 |
| 2011/0306989 A1 | 12/2011 | Darois et al. | |

OTHER PUBLICATIONS

International Preliminary Report and Written Opinion for PCT/US2013/074564, dated Jun. 23, 2015, 11 pp.

Annex Form PCT/ISA/206 (Patent Family Annex) to International Application No. PCT/US2013/074564, dated Mar. 3, 2014, 1 page.

International Search Report and Written Opinion for PCT/US2013/074564, dated Apr. 7, 2014, 18 pages.

* cited by examiner

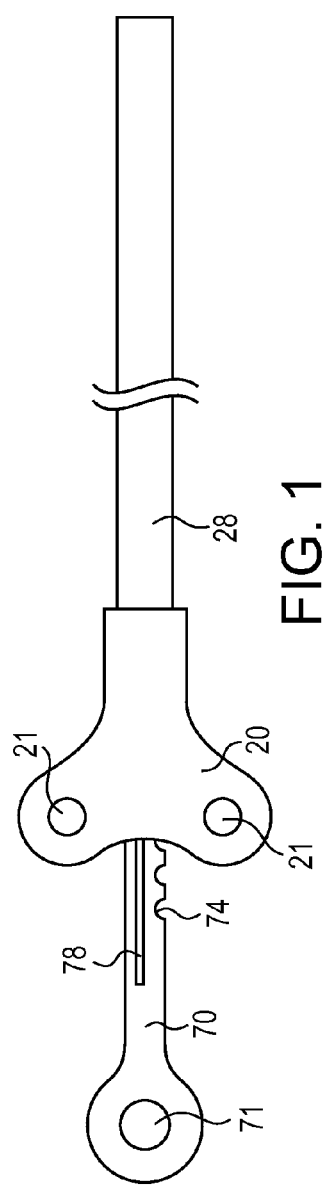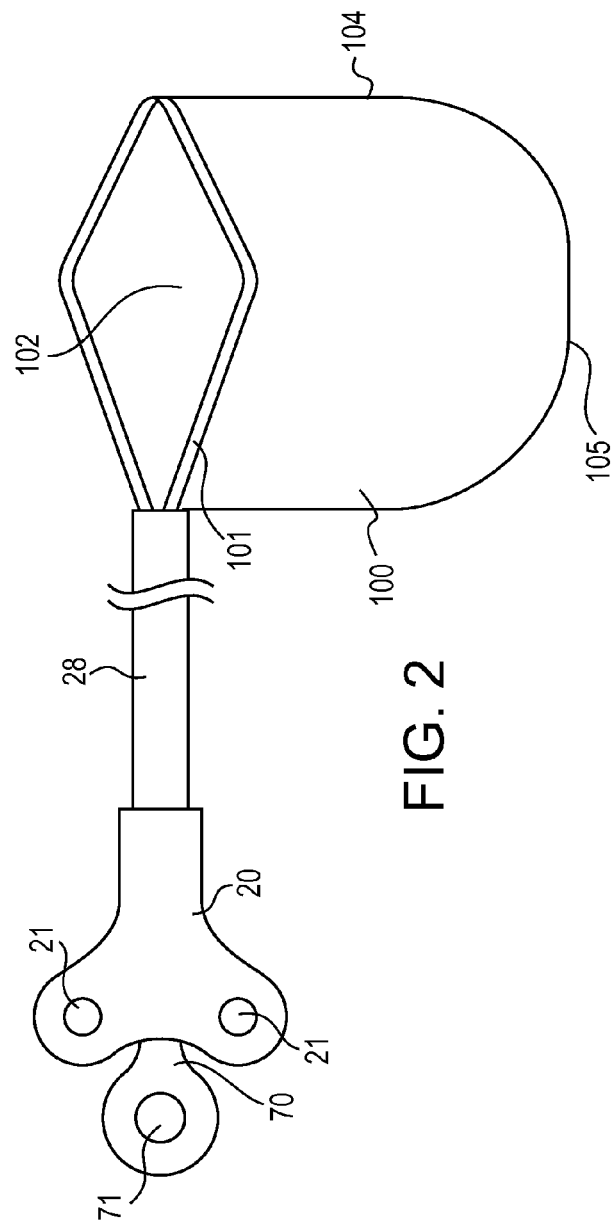

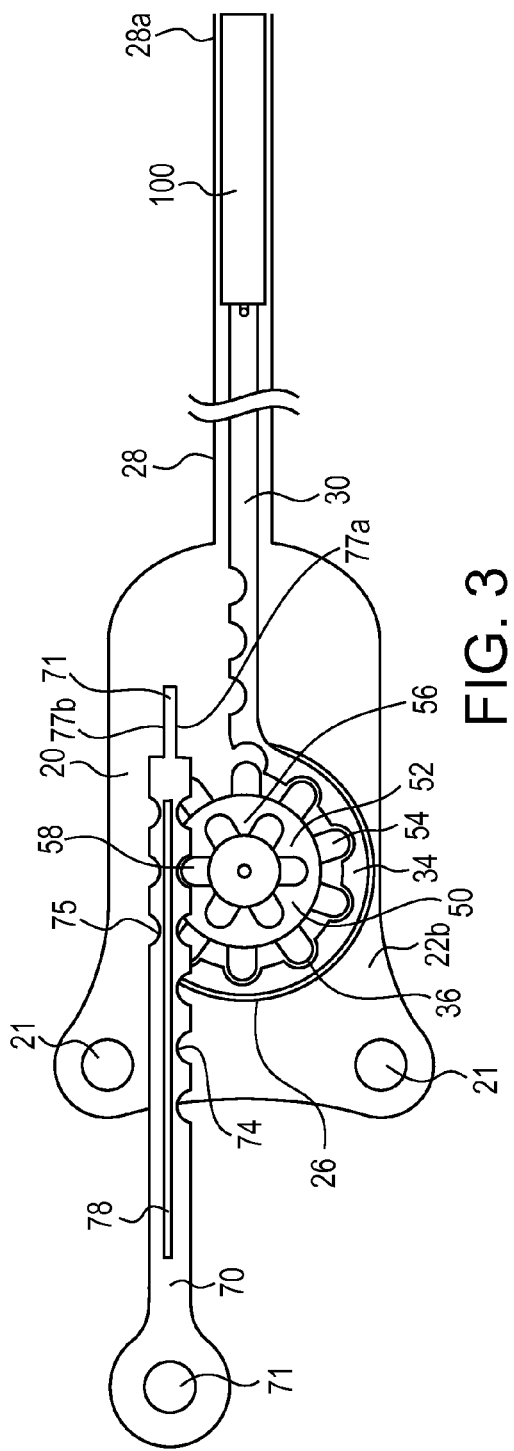
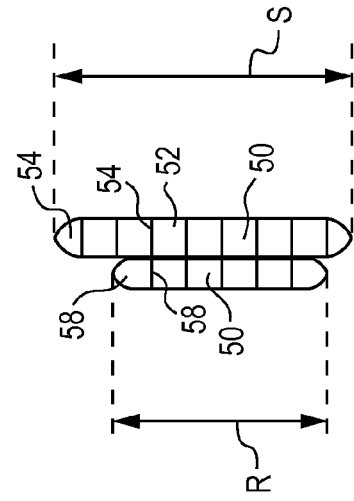
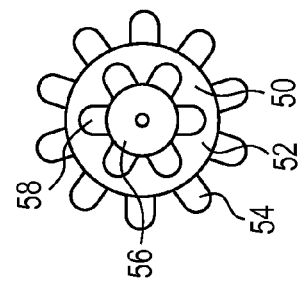
FIG. 3
FIG. 5
FIG. 4

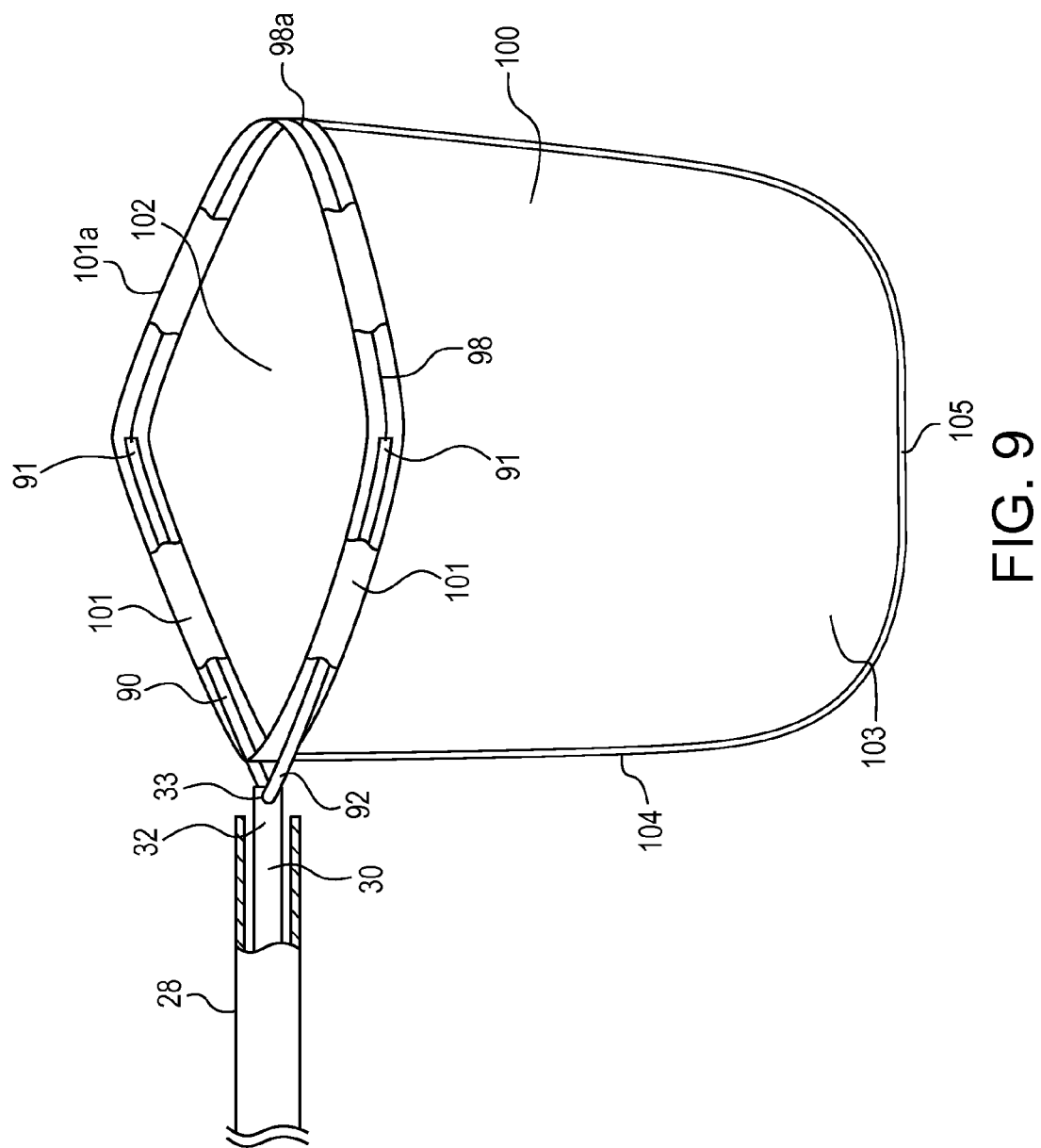

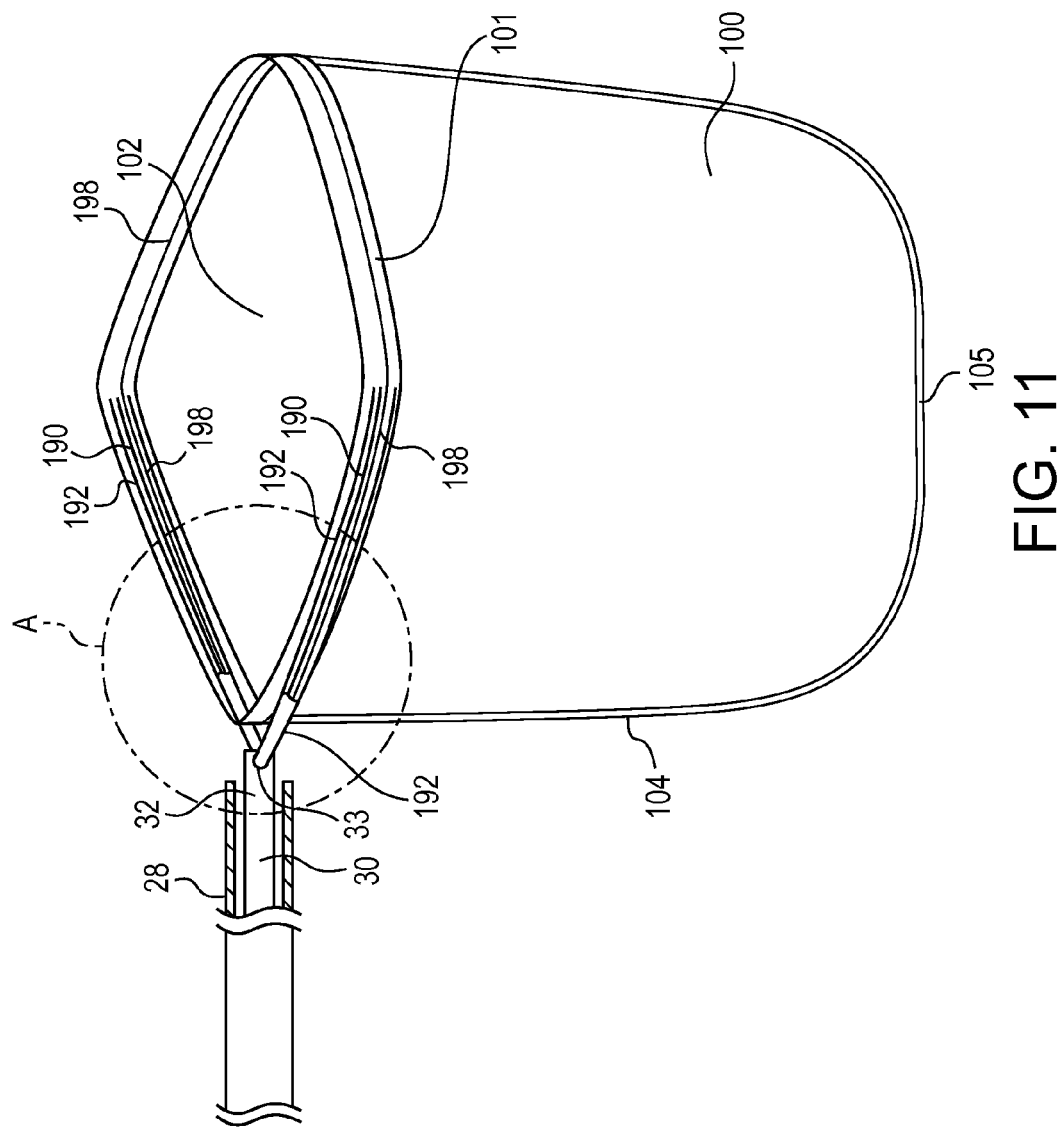

SURGICAL BAG DEVICE AND REMOTE OPERATING MECHANISM

CROSS-REFERENCE TO RELATED APPLICATIONS

This application claims priority from U.S. Provisional Application No. 61/745,004, filed on Dec. 21, 2012, the entirety of which is hereby fully incorporated by reference herein.

TECHNICAL FIELD

Laparoscopic procedures are frequently performed in patients (humans or mammals) to remove or modify a patient's tissue or anatomy in a minimally invasive manner, which allows for achievement of the clinical goal of the procedure while limiting the amount of surgical cutting or other trauma to the patient normally associated with open surgery. Laparoscopic procedures are normally associated with multiple small incisions made into the patient wherein tools may be passed through the small incisions to the surgical field through ports that are placed at each incision. Often it is clinically necessary to remove tissue from a patient during the procedure, which is placed into a surgical bad disposed at the surgical site for receipt of the tissue to be removed. The subject disclosure relates to surgical bag devices that are remotely operated and are configured to be used through or in conjunction with laparoscopic ports, or through open surgery.

BRIEF SUMMARY

A first representative embodiment of the disclosure is provided. The first embodiment includes a flexible material forming a bag with side and bottom seams defining a volume therein and an open top portion defining an aperture to allow access into the volume. The open top comprises a pocket disposed along substantially along an entire outer circumference of the open top. An elongate biasing member is disposed in conjunction with the pocket and translatable between a first open position where the biasing member extends through a substantial portion of a circumference of the pocket, to a second closed position where the biasing member is withdrawn from the pocket. An elongate push rod with a distal end portion is fixed to the biasing member and an opposite proximal end portion operatively engaged with a movable plunger within a housing, wherein the push rod is translatable as urged by the plunger such that the push rod is extendable to a distal position directing the biasing member into the open first position, and the push rod is translatable to a proximal position that urges the biasing member into the second position. The plunger comprises a ledge that extends along a length of a distal portion thereof, and the housing comprises a recess disposed therein to receive the ledge when the plunger is in the first position rotational position with respect to the housing, wherein the recess is sized to allow for a full range of motion of the plunger with respect to the housing for the basing member to translate between the first and second positions.

A second representative embodiment of the disclosure is provided. The second embodiment includes a flexible material forming a bag with side and bottom seams defining a volume therein and an open top portion defining an aperture to allow access into the volume, the open top comprises a pocket disposed along substantially along an entire outer circumference of the open top. An elongate biasing member is disposed in conjunction with the pocket and translatable between a first open position where the biasing member extends through a substantial portion of a circumference of the pocket, to a second closed position where the biasing member is withdrawn from the pocket. An elongate push rod with a distal end portion is fixed to the biasing member and an opposite proximal end portion operatively engaged with a movable plunger within a housing, wherein the push rod is translatable as urged by the plunger such that the push rod is extendable to a distal position directing the biasing member into the open first position, and the push rod is translatable to a proximal position that urges the biasing member into the second position. The push rod comprises a plurality of longitudinally spaced teeth disposed thereon, which are meshingly engageable with a plurality of teeth from a corresponding first set of teeth of a pinion gear.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 is a side view of a surgical bag deployment device with the surgical bag disposed within the outer sheath of the device.

FIG. 2 is the view of FIG. 1 with the surgical bag deployed from the outer sheath.

FIG. 3 is the view of FIG. 1 with the first clamshell half removed.

FIG. 4 is a top view of the pinion of the device of FIG. 1.

FIG. 5 is a side view of the pinion of FIG. 1.

FIG. 9 is a perspective view of the surgical deployed surgical bag of the device of FIG. 1 and a distal end portion of the outer sheath.

FIG. 11 is a perspective view of an alternate surgical bag that may be used with the device of FIG. 1 and the distal end portion of the outer sheath.

DETAILED DESCRIPTION OF THE DRAWINGS AND THE PRESENTLY PREFERRED EMBODIMENTS

Figure 6:
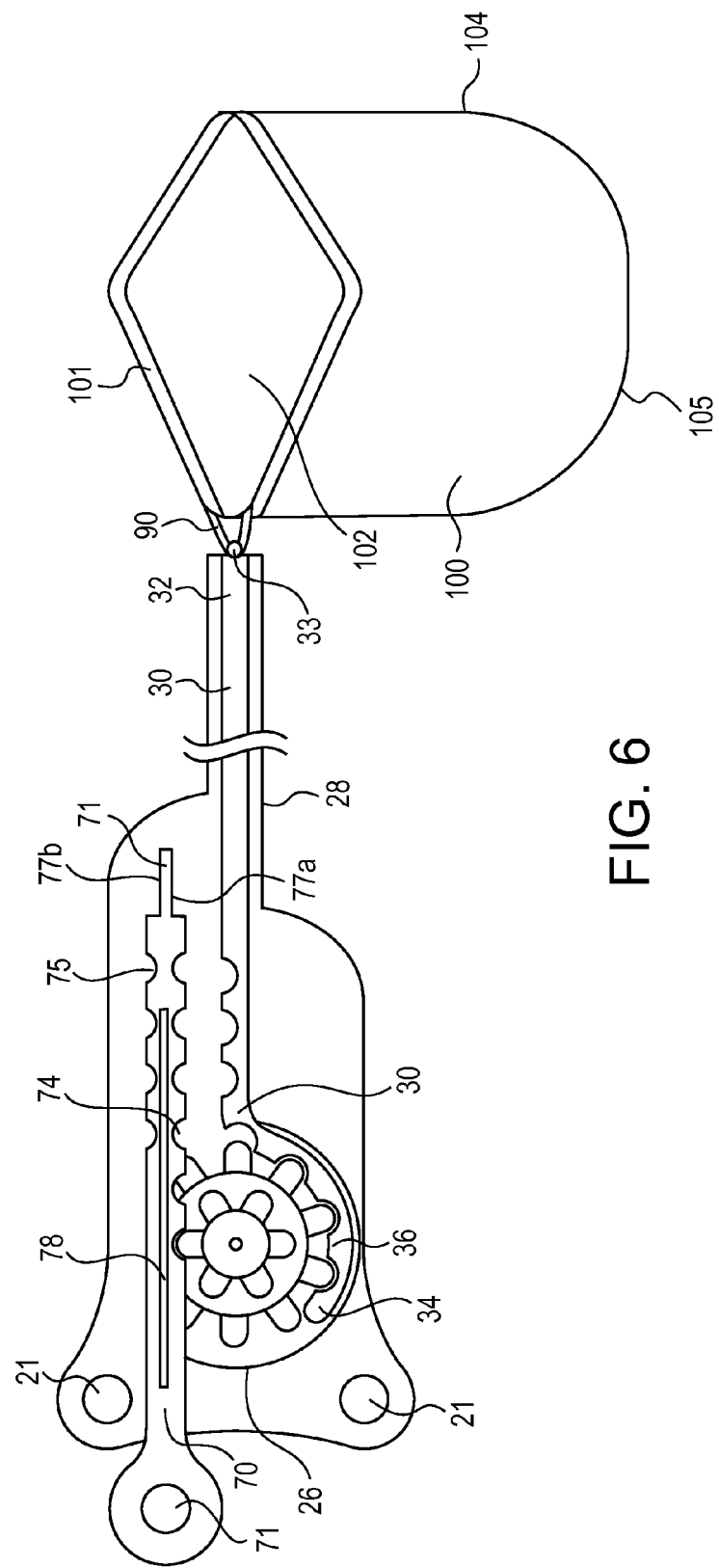
FIG. 6 is a perspective view of the surgical bag deployment device of FIG. 1 with the first clamshell half removed and depicting a sectional view of the outer sheath.

Turning now to FIGS. 1-10b, a surgical bag deployment device 10 is provided. The device 10 includes an outer sheath 28, a housing 20 that may include one, two, or more finger holes 21 for supporting with a medical practitioner's hand, a plunger 70 that slidingly engages the housing 20, and a push rod 30 that is slidably mounted within the sheath 28 and housing 20 with movement of the push rod 30 urged by movement of the plunger 70 by way of a pinion 50, or other force transmission structure. The push rod 30 supports a biasing member 90 at a distal end 32 of the push rod 30. The biasing member 90 selectively extends through a portion of a pocket 101 formed around a portion of the outer circumference of an open top 102 of a flexible pocket as the plunger 70 is translated distally with respect to the housing 20, or bag 100 and may be withdrawn from the pocket 101 as the plunger 70 is translated proximally from the housing 20.

The housing 20 may be formed from two clamshell halves 20a, 20b (FIGS. 10a and 10b, respectively) and includes two or more holes 21 for supporting and orienting the housing 20 and the remainder of the device 10. In some embodiments, the housing slidably receives both the plunger 70 and the push rod 30, and may rotatably receive the pinion 50, which selectively meshes simultaneously with the push rod 30 and the plunger 70. In some embodiments, the housing 20 may include a first elongate recess 24a in the first clamshell half 20a of the housing 20 and may include a second elongate recess 24b in the second clamshell half 20b of the housing 20, which are each configured to receive a ledge 78 disposed upon the plunger 70, discussed below.

The housing 20 may include a first track 25 for slidably supporting the plunger 70 and a second track 26 for slidably receiving the push rod 30. In some embodiments, the first track 25 is disposed within the first clamshell half 20a, and the second track 26 is disposed within the second clamshell half 20b. The first track 25 may be substantially straight, while the second track 26 may include an arcuate portion 26a and a straight portion 26b. The arcuate portion 26a is formed with a radius just larger than the radius of the first wheel 52 of the pinion 50 and surrounds a substantial portion of the circumference of the pinion 50, such as 90, or 120, or 150, or 180 degrees of arc length (or any other suitable arc length) to provide for a mesh between a substantial number of teeth 54 of the first wheel 52 of the pinion 50 and a corresponding teeth 36 of the push rod 30 (each discussed in additional detail below) to cause the push rod 30 to translate within the second track 26 and the sheath 28 when the pinion 50 rotates. In some embodiments, the arcuate orientation of the second track 26 allows for a substantial potential translation distance of the push rod 30, while minimizing the size of the housing 20 (than would be necessary if the second track 26 were straight).

The first track 25 receives and slidably supports the plunger 70 to maintain one or more teeth 74 of the plunger 70 meshed with a corresponding number of teeth 58 the second wheel 56 of the pinion 50. In some embodiments, the housing 20 is sized to maintain the distal end portion 71 of the plunger completely therein throughout the complete range of translation of the plunger 70 with respect to the housing 20, while in other embodiments, the distal end portion 71 of the plunger 70 may extend into the sheath 28 as the plunger 70 is translated toward and reaches the second position (FIG. 6) where the bag is fully deployed from the sheath 28 and fully open. In some embodiments, the first track 25 may include the first elongate recess 24a defined therealong, which receives a corresponding ledge 78 of the plunger 70, when the plunger 70 is in the first configuration (FIGS. 1 and 2) with respect to the housing 20 to allow for a full range of motion of the plunger 70 with respect to the housing 20. In these embodiments, the second clamshell half 20a may include a third track 27 that slidably receives and supports the plunger 70 for longitudinal motion within the housing 20. The third track 27 may include a second elongate recess 24b disposed blindly therealong, which receives the ledge 78 of the plunger 70, when the plunger is in the third configuration (FIG. 8c) with respect to the housing 20, as discussed below. As discussed in greater detail below, the second elongate recess 24b is defined blindly along the third track 27, and has a shorter length than the first elongate recess 24a, such that the plunger 70 cannot extend the same distance with respect to the housing 20 when the plunger 70 is disposed in the third configuration. As discussed below, and understood with reference to FIGS. 8a-8c and 10a-10b, the engagement between the distal edge of the ledge 78 and the distal end 24c of the second elongate recess 24b prevents further distal sliding of the plunger 70 with respect to the housing 20. In other embodiments, one or both of the first elongate recess 24a and the second elongate recess 24b may be formed on the respective first and second clamshell half 20a, 20b and not be associated or included with other structure in the housing, such as the first or third tracks 25, 27.

The pinion 50 includes a first wheel 52 and a coaxial second wheel 56 that are fixedly mounted together and rotate simultaneously along a single axis 59. The first and second wheels 52, 56 each have a plurality of teeth 54, 58 that are disposed consistently along the outer circumference of each wheel. As discussed above the teeth 58 of the second wheel 56 are configured to mesh with corresponding teeth 74 disposed upon the plunger 70 and the teeth 54 of the first wheel 52 are configured to mesh with teeth 36 disposed upon the arcuate proximal end portion 34 of the push rod 30.

In some embodiments and as best shown in FIG. 5, the diameter R of the second wheel 56 of the pinion 50 is smaller than the diameter S of the first wheel 52 of the pinion 50. Due to the different diameters for the first and second wheels 52, 56 the teeth 54 of the first wheel 52 travel a greater distance than the teeth 58 of the second wheel 56 as the pinion 50 rotates. Therefore, as the plunger 70 moves a given distance (either in a distal direction or in a proximal direction) the push rod 30 is urged to move a larger distance due to the larger diameter of the first wheel 52 meshed with push rod 30. Accordingly, the range of the motion of the plunger 70 needed to fully open and close the pocket 100 (by way of the motion of the push rod 30) is a function of the ratio of the diameters S, R of the first and second wheels 52, 56 and the length of motion of the push rod 30 needed to fully open and close the open top 101 of the bag 100. In some embodiments, the ratio of diameters of S:R (the gear ratio) may be 1.25:1, 1.5:1, 2:1, or other suitable ratios (which would be easily understood by one of ordinary skill in the art after review of this disclosure) based upon the desired sizes of the bag 100 and the desired throw length of the plunger 70. In some embodiments, the gear ratio and the length of the plunger 70 are configured to allow the bag 100 transferred between a position with the open top 102 fully opened (FIG. 2) and the open top 102 fully closed, or cinched (FIG. 8) with a single hand of the medical professional, with the professional's thumb engaging the ring 72 of the plunger 70 and the professional's index and middle fingers engaging the two rings 21 (or apertures) in the housing 20.

Figure 7:
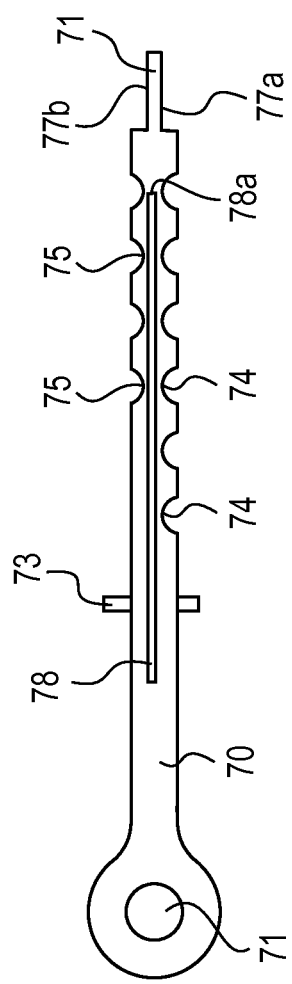
FIG. 7 is a side view of the plunger of the device of FIG. 1.

As shown in FIG. 7, the plunger 70 may include a first set of teeth 74 disposed therealong that are configured to mesh with the teeth 58 of the second wheel 56 of the pinion 50 when the plunger 70 is in the first configuration (FIG. 6) with respect to the housing 20, and a second set of teeth 75 disposed upon the opposite surface of the plunger 70 from the first set of teeth 74. The second set of teeth 75 are configured to mesh with the teeth 58 of the second wheel 56 of the pinion 50 when the plunger 70 is in the third configuration (FIG. 8c) with respect to the housing 20. In some embodiments, there may be less teeth in the second set of teeth 75 than the first set of teeth 74 because the plunger 70 cannot translate within the housing 20 as far when in the third configuration due to the engagement of the ledge 78 and the edge of the second elongate recess 24b in the housing 20, which limits the travel of the plunger 70 with respect to the housing 20 (and therefore allows the open top 102 of the bag 100 to be partially opened but prevents the open top 102 from fully opening when the plunger 70 is in the third configuration).

Figure 8A:
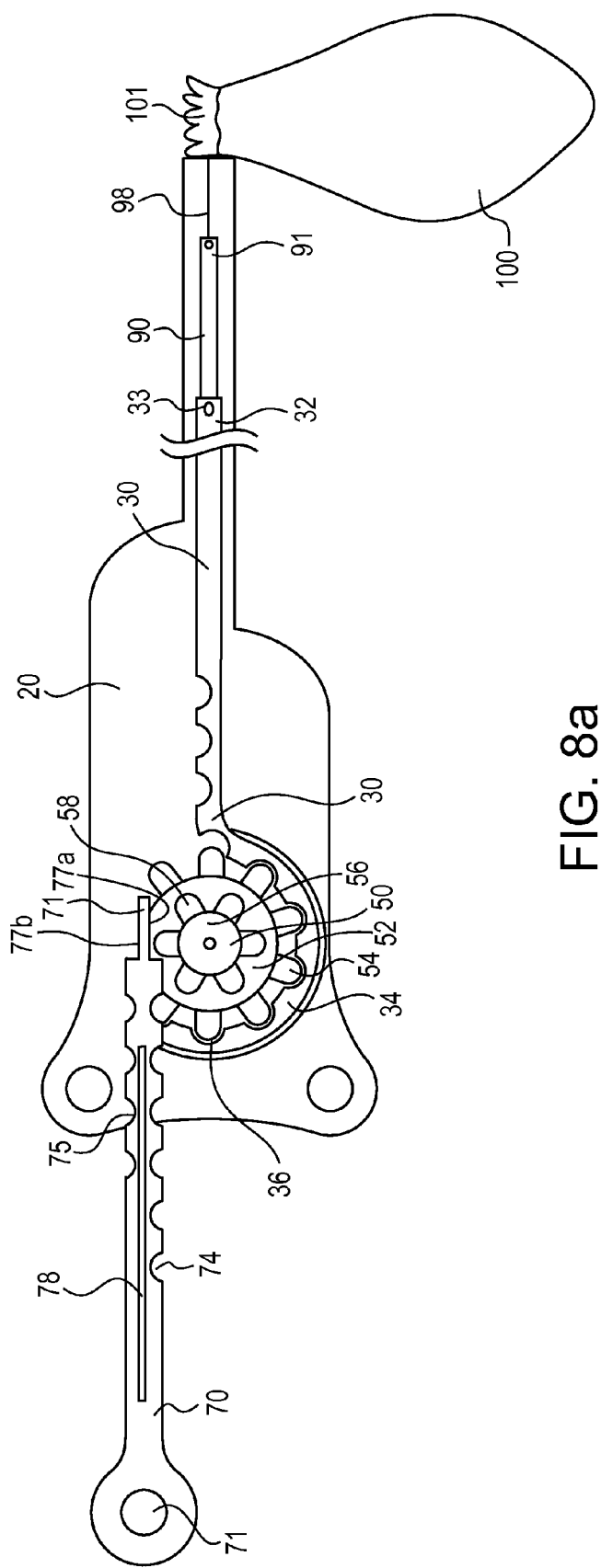
FIG. 8a is a side view of the device of FIG. 3 with the surgical bag in the cinched configuration and the plunger in the first configuration.
Figure 8B:
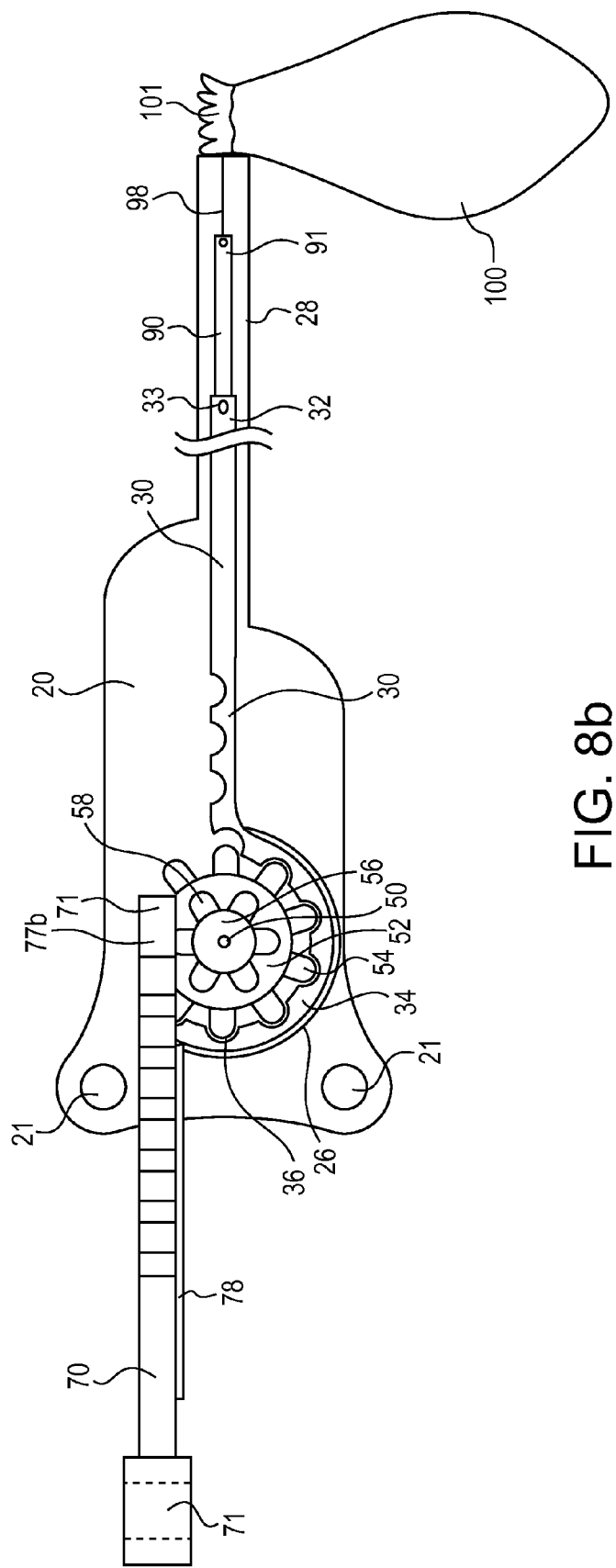
FIG. 8b is the view of FIG. 8a with the plunger in the second configuration.
Figure 8C:
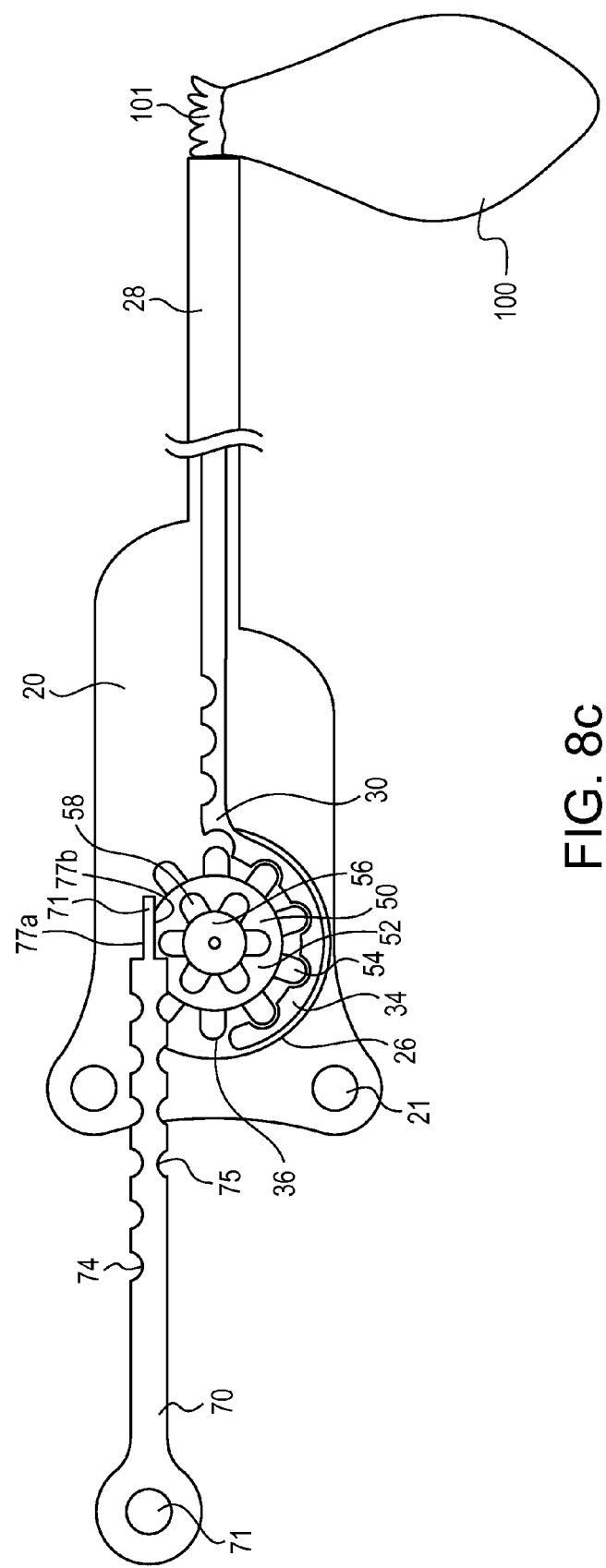
FIG. 8c is the view of FIG. 8a with the plunger in the third configuration.
Figure 10B:
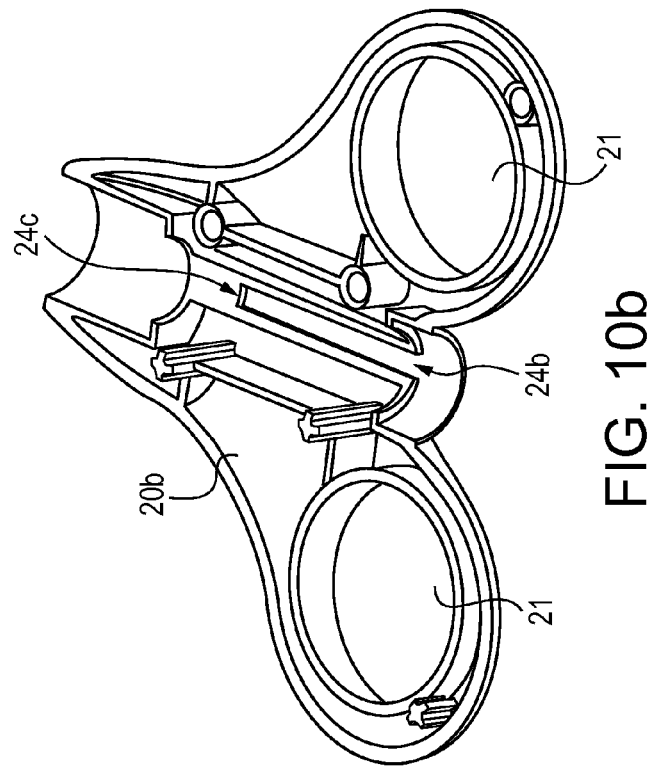
FIG. 10b is a perspective view of the second clamshell half of the device of FIG. 1.
Figure 10A:
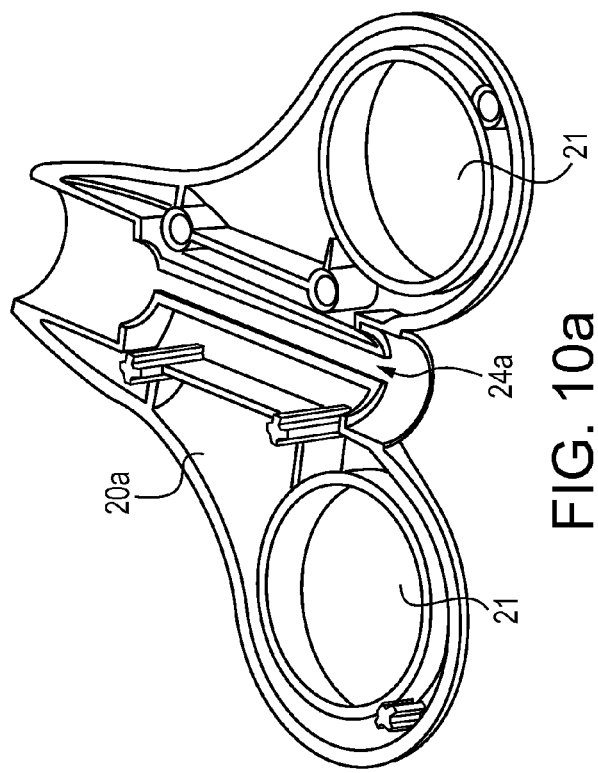
FIG. 10a is a perspective view of the first clamshell half of the device of FIG. 1.
Figure 10C:
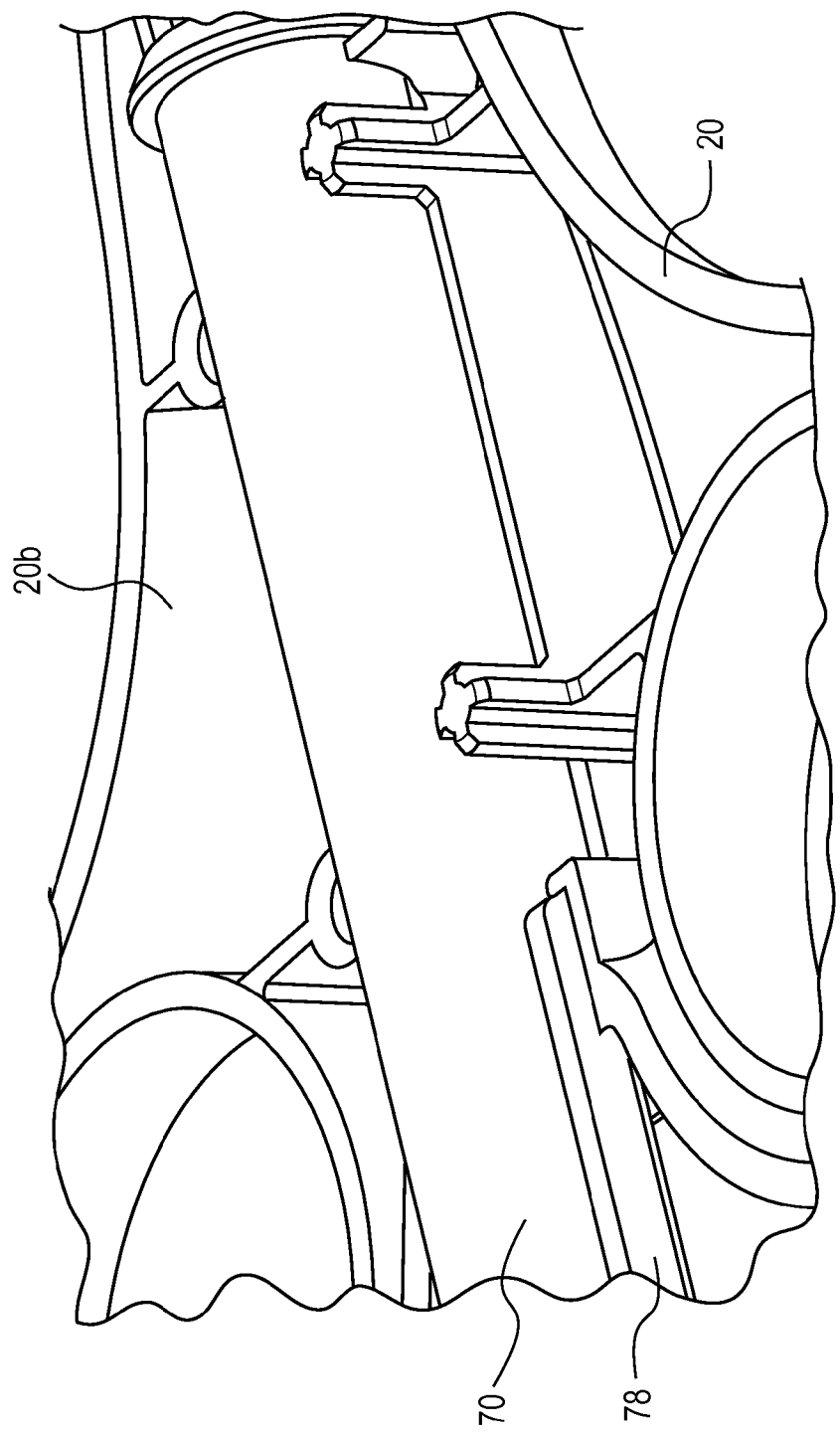
FIG. 10c is a perspective view of the ledge of the plunger interacting with the housing when the device is in the third configuration.

In some embodiments, the distal end portion 71 of the plunger 70 may include one or both of first and second cutouts 77a, 77b. As shown in FIG. 8a-8c, the cutouts 77a, 77b are configured to establish clearance between the teeth 58 of the second wheel 56 of the pinion 50 and the plunger 70 to allow the plunger 70 to be rotated along its axis W. As understood when compared to FIG. 6, in some embodiments, the plunger 70 may not be rotatable with respect to the housing when the teeth 74, 75 of the plunger 70 mesh with teeth 58 of the second wheel 56 of the pinion 50. The plunger 70 is rotatable about its axis when the plunger is in the fully withdrawn (or fully proximal) position, which may be constrained by engagement between a block 73 on the plunger 70 and the housing 20 or similar structure to prevent the plunger 70 from being fully withdrawn from the housing 20.

As discussed above, range of distal motion of the plunger 70 is constrained when in the third configuration due to the engagement of the distal tip 78a of the ledge 78 and the distal end of the second elongate recess 24b. The third configuration of the plunger 70 may be substantially opposite from the first configuration of the plunger 70 (e.g. about 180 degrees of rotation apart), where the ledge 78 travels within the first elongate recess 24a in the housing 20 for full travel of the plunger 70 therewithin, which, as mentioned above, allows for full opening of the open top 101 of the bag 100. In some embodiments, the plunger 70 may be rotatable to a second configuration between the first and third configurations, as shown in FIG. 8b. The second configuration may be at a rotational position of the plunger 70 of about 90 degrees between both of the first and third configurations, while in other embodiments the second configuration may be at other rotational positions of the plunger 70 with respect to the housing 20 between the first and second configurations, such as at about 45 degrees from the first configuration, about 45 degrees from the third configuration, or the like. In some embodiments, the plunger 70 and the housing 20 may have corresponding locating features (such as structural locating features on one or both of the plunger 70 and housing 20 and/or visual or tactile locating features) that urge the plunger 70 into the desired first, second, or third configuration, for ease of use of manipulation of the medical professional. The housing 20 is defined without a recess to receive the ledge 78 when the plunger is in the second configuration, such that the plunger 70 cannot be advanced distally within the housing 20. Accordingly, the bag 100 is "locked" in the closed or cinched configuration, discussed below, when the plunger 70 is in the second configuration.

In some embodiments, the device 10 may be configured such that the plunger 70 may include both the ledge 78 that extends within one of the respective first and second elongate recesses 24a, 24b when the plunger 70 is in the first and third configuration, respectively, and may include one or both of the of the first and second sets of teeth 74, 75 for meshing with the teeth 58 of the second wheel 56 of the pinion 50, for transmitting the input force of the plunger 70 to the push rod 30 for opening or closing the open top 101 of the bag 100. In other embodiments, the device 10 may configured such that the plunger 70 does not include the ledge 78, and the rotational position of the plunger 70 may be fixed with respect to the housing 20 for continuous engagement with the second wheel 56 of the pinion 50. In still other embodiments, the plunger 70 may include the ledge 78 or other similar structure that is engagable with first and second elongate recesses 24a, 24b when in the first and third configurations (and may also not mate with a corresponding recess when the in the intermediate second position) to selectively limit the translation of the plunger 70 with respect to the housing 20 while the motion (and force) of the plunger 70 is ultimately transmitted to the push rod 30 (or similar structure movable within the sheath 28) to open and close the bag 100 through another type of transmission mechanism.

With reference to FIGS. 1, 6, and 9, the surgical sleeve or bag 100 is provided. The bag 100 includes an open top 102 that allows for access to an internal volume defined by two opposite 103 of the bag 100 that are fixed together at side seams 104 and a bottom seam 105. The open top 102 of the bag 100 includes a pocket 101 that defines an upper edge 101a that travels around the entire open circumference of the bag 100. The pocket 101 allows an elongate object to travel through the pocket 101 along the entire circumference of the bag (if desired). FIG. 9 depicts the pocket with portions of the respective inner or outer surface of the pocket 101 removed to depict a biasing member 90 and a suture 98 extending therearound (collectively).

The biasing member 90 may be an elongate wire, sheet, bar, or the like, and includes two extended end portions 91 and a central portion 92 that is threaded through a hole 33 disposed in the distal end portion 32 of the push rod 30. The opposite end portions 91 of the biasing member 90, and the majority of the remainder of the biasing member 90 up to the central portion 92 are disposed through opposite sides of the pocket 101 when the bag 100 is in the open position, as shown in FIGS. 2 and 9. The biasing member 90 may be a flexible and high strain material such as a superelastic or a shape memory material, and is configured to continuously attempt to be oriented in a substantially straight configuration along its length. The walls of the pocket 101 (or the sheath 28 when the biasing member 28 is withdrawn proximally from the pocket 101) constrain the opposite end portions 91 of the biasing member 90, with the biasing force of the opposite end portions 91 of the biasing member 90 causing the open top 102 of the bag to open as much as possible for access to the internal volume of the bag 100 (as constrained by the side and bottom seams 104, 105), such that the bag 100 is in the open position (FIG. 2, 6) when the opposite end portions 91 of the biasing member 90 extend within opposite portions of the pocket 101.

The suture 98 is an elongate member that is threaded through the pocket 101, and opposite ends of the suture 98 may be connected to the opposite end portions 91 of the biasing member 90. Accordingly, as can be appreciated with reference to FIG. 9, a portion of the suture 98 always extends through at least a portion of the pocket 101. Specifically, when the bag 100 is in the open position, the entire suture 98 extends around a portion of the circumference of the pocket 101 between the opposite end portions 91 of the biasing member 90, and when the bag 100 is in the cinched closed position (FIG. 8), a central portion of the suture 98a remains within the pocket 101 (which is cinched closed) and the remainder of the suture 98 and the entire biasing member 90 is withdrawn into the sheath 28.

Figure 11A:
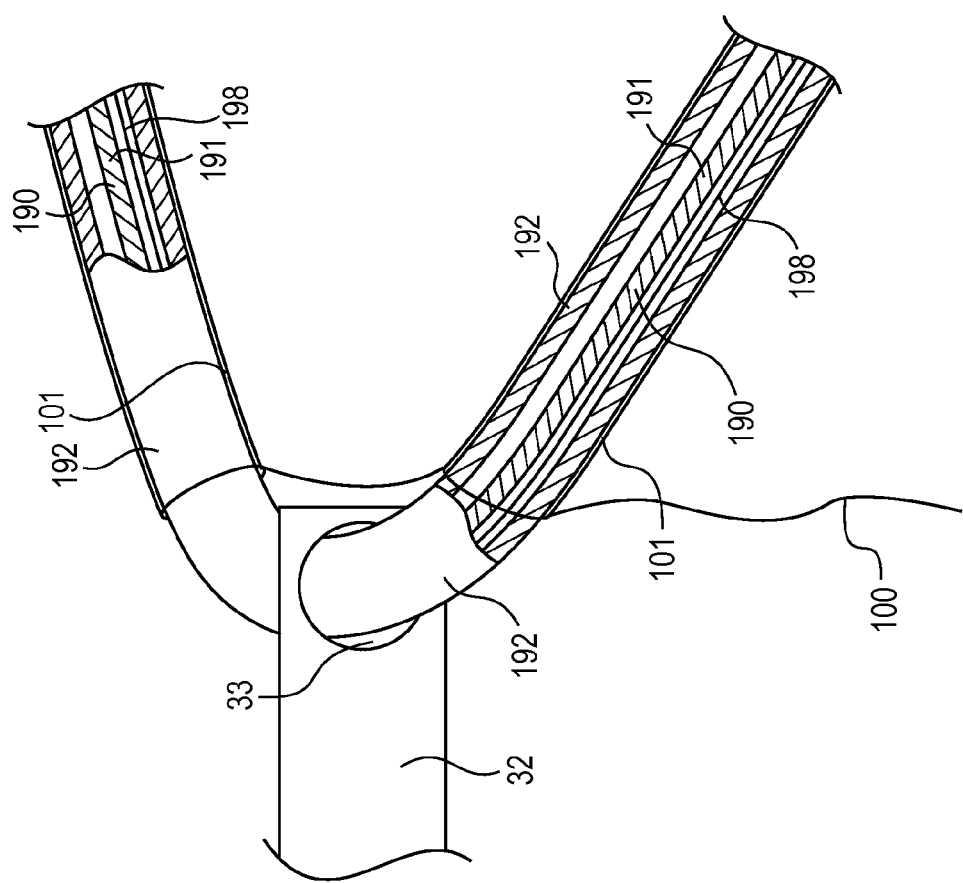
FIG. 11a is a detail view of detail A of FIG. 11.

In other embodiments as shown in FIGS. 11 and 11a, a biasing member 190 may be slidably received within a tube 192 that extends through the hole 33 in the distal end portion 32 of the push rod 30. The tube 192 receives the biasing member 190 therethrough such that the biasing member 190 also extends through the hole 33 in the push rod 30 (and the tube 192 and biasing member 190 have opposite portions 191 that extend through a portion on each opposite side of the pocket 101 of the bag 100. As with the biasing member 90 discussed above, the biasing member 190 is trained to be biased toward a straight configuration, which causes the open top 102 of the bag 100 to extend to an open configuration (FIG. 11) when the opposite portions 191 of the biasing member 190 extend within the opposite portions of the pocket 101. A suture 198 may additionally extend through the entire circumference of the pocket 101 and make a loop with a portion that extends through the tube 192 (and therefore through the hole 33 in the push rod 30 (by way of the tube 192). Similar to the embodiment discussed above, when the push rod 30 is in the distal position within the sheath 28, the open top 102 of the bag 100 is urged to the open position by outward extension of the biasing member 190 within the pocket 101, and when the push rod 30 is in the proximal position, the biasing member 190 (and tube 192) are withdrawn proximally from the pocket 101 and the suture 198 is similarly pulled proximally such that the pocket 101 of the bag 100 is cinched shut.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A surgical bag device, comprising:
a flexible material forming a bag with side and bottom seams defining a volume therein and an open top portion defining an aperture to allow access into the volume, the open top comprising a pocket disposed along substantially along an entire outer circumference of the open top;
an elongate biasing member disposed in conjunction with the pocket and translatable between a first open position where the biasing member extends through a substantial portion of a circumference of the pocket, to a second closed position where the biasing member is withdrawn from the pocket;
an elongate push rod with a distal end portion fixed to the biasing member and an opposite proximal end portion operatively engaged with a movable plunger within a housing, wherein the push rod is translatable as urged by the plunger such that the push rod is extendable to a distal position directing the biasing member into the open first position, and the push rod is translatable to a proximal position that urges the biasing member into the second position,
wherein the push rod comprises a plurality of longitudinally spaced teeth disposed thereon, which are meshingly engagable with a plurality of teeth from a corresponding first set of teeth of a pinion gear,
wherein the housing supports and encloses an engagement between the pinion gear and the push rod and an engagement between the plunger and the pinion gear, wherein the plunger is rotatable about its longitudinal axis,
wherein the plunger comprises a ledge defined blindly along and in parallel with the longitudinal axis of the plunger, the ledge extends radially from a side surface of the plunger, and the housing comprises an elongate first slot configured to receive the ledge when the plunger is in a first rotational position, wherein sliding engagement between the ledge and the first slot allows a full range of motion of the plunger with respect to the housing, such that the biasing member may translate between the first and second positions,
wherein the ledge does not extend within the recess within the housing when the plunger is rotated to a different second rotational position, wherein rotation of the plunger to the second rotational position prevents the plunger from moving distally with respect to the housing.

2. The surgical bag device of claim 1, wherein the pinion comprises a first wheel that supports the first set of teeth, and a coaxial second wheel that supports a second set of teeth, wherein a radius of the first wheel is greater than a radius of the second wheel.

3. The surgical bag device of claim 2, wherein the plunger comprises a first plurality of longitudinally spaced first plunger teeth disposed thereon, the first plunger teeth are engagable with corresponding teeth of the second set of teeth of the pinion, such that longitudinal motion of the plunger causes longitudinal motion of the push rod in the same direction as the plunger.

4. The surgical bag device of claim 3, wherein the plunger is translatable between a proximal position wherein the push rod is urged to a proximal position within the sheath by way of the pinion thereby withdrawing the biasing member from the pocket and a distal position where the push rod is in a distal position and the biasing member is threaded through the pocket.

5. The surgical bag device of claim 4, wherein the open top allows access into the internal volume when the plunger is in the distal position, and the open top is substantially closed to prevent access to the internal volume when the plunger is in the proximal position.

6. The surgical bag device of claim 3, wherein the radius of the first wheel and the radius of the second wheel are each selected such that a distance of longitudinal motion of the push rod is larger than a distance of longitudinal motion of the plunger by a proportion of greater than one.

7. The surgical bag device of claim 1, wherein the housing supports and encloses an engagement between the pinion gear and the push rod and an engagement between the plunger and the pinion gear.

8. The surgical bag device of claim 1, wherein the housing comprises a second slot defined on an opposite portion of the housing from a portion of the housing that defines the first slot, wherein a length of the second slot is less than a length of the first slot, wherein the plunger is rotatable with respect to the housing to a third rotational position for sliding engagement between the ledge and the second slot.

9. The surgical bag device of claim 8, wherein the plunger comprises a second set of a plurality of teeth disposed along a longitudinal surface of the plunger opposite from the first set of plunger teeth, wherein the second set of a plurality of teeth engage the second set of teeth of the pinion gear when the ledge engages the second slot in the housing.

10. The surgical bag device of claim 8, wherein the sliding engagement between the ledge and the second slot allows for a partial range of motion of the plunger with respect to the housing, such that the open top of the pocket only partially opens with full possible distal motion of the ledge of the plunger with respect to the second slot of the housing.

11. The surgical bag device of claim 8, wherein the second rotational position between the first and third rotational positions.

12. The surgical bag device of claim 11, wherein the biasing member is maintained in the second closed position when the plunger is in the second rotational position, such that the open top is substantially cinched to prevent access to the internal volume when the biasing member is in the second closed position.

13. A surgical bag device, comprising:
a flexible material forming a bag with side and bottom seams defining a volume therein and an open top portion defining an aperture to allow access into the volume, the open top comprising a pocket disposed along substantially along an entire outer circumference of the open top;
an elongate biasing member disposed in conjunction with the pocket and translatable between a first open position where the biasing member extends through a substantial portion of a circumference of the pocket, to a second closed position where the biasing member is withdrawn from the pocket;
an elongate push rod with a distal end portion fixed to the biasing member and an opposite proximal end portion operatively engaged with a movable plunger within a housing, wherein the push rod is translatable as urged by the plunger such that the push rod is extendable to a distal position directing the biasing member into the open first position, and the push rod is translatable to a proximal position that urges the biasing member into the second position,
wherein the push rod comprises a plurality of longitudinally spaced teeth disposed thereon, which are meshingly engagable with a plurality of teeth from a corresponding first set of teeth of a pinion gear, wherein the proximal portion of the push rod is configured to travel along an arcuate path within the housing for engagement between the teeth of the push rod and the first set of teeth of the pinion around a substantial portion of a circumference of the pinion.

14. The surgical bag device of claim 13, wherein the proximal end portion of the push rod is sufficiently flexible to retain both arcuate and straight configurations depending upon the relative position of the push rod with respect to the pinion.

15. A surgical bag device, comprising:
a flexible material forming a bag with side and bottom seams defining a volume therein and an open top portion defining an aperture to allow access into the volume, the open top comprising a pocket disposed along substantially along an entire outer circumference of the open top;
an elongate biasing member disposed in conjunction with the pocket and translatable between a first open position where the biasing member extends through a substantial portion of a circumference of the pocket, to a second closed position where the biasing member is withdrawn from the pocket;
an elongate push rod with a distal end portion fixed to the biasing member and an opposite proximal end portion operatively engaged with a movable plunger within a housing, wherein the push rod is translatable as urged by the plunger such that the push rod is extendable to a distal position directing the biasing member into the open first position, and the push rod is translatable to a proximal position that urges the biasing member into the second position,
wherein the plunger comprises a ledge that extends along a length of a distal portion thereof, and the housing comprises a recess disposed therein to receive the ledge when the plunger is in a first rotational position with respect to the housing, wherein the recess is sized to allow for a full range of motion of the plunger with respect to the housing for the biasing member to translate between the first and second positions,
wherein the ledge does not extend within the recess within the housing when the plunger is rotated to a different second rotational position, wherein rotation of the plunger to the second rotational position prevents the plunger from moving distally with respect to the housing.

16. The surgical bag device of claim 15, wherein the housing further comprises a second recess disposed upon a second housing portion substantially opposite from a first portion of the housing that defines the first recess, wherein the second recess extends for a length less than a length of the first recess, wherein engagement between the ledge and the second recess limits a range of distal travel of the plunger with respect to the housing to prevent the biasing member from reaching the first open position, wherein the ledge slides within the second recess when the plunger is in a third rotational position.

17. The surgical bag device of claim 16, wherein the plunger is rotatably mounted to the housing for rotation about its longitudinal axis, wherein the plunger is rotatable between the first and third positions allowing engagement of the ledge with the respective first or second recesses.

18. The surgical bag of claim 15, wherein the plunger is rotatably mounted to the housing for rotation about its longitudinal axis, wherein the plunger is rotatable with respect to the housing between the first and second positions when the plunger is withdrawn proximally from the housing such that the ledge upon the piston is not extending within the recess.

19. The surgical bag of claim 17, wherein the plunger is rotatable with respect to the housing between its first, second, and third positions when the plunger is withdrawn proximally from the housing such that the ledge upon the piston is not extending within either of the recess or the second recess.

20. The surgical bag of claim 15, wherein the ledge extends radially from a side surface of the plunger.

* * * * *